United States Patent [19]

Urano et al.

[11] Patent Number: 4,925,982
[45] Date of Patent: May 15, 1990

[54] PRODUCTION OF ISOCYANATE COMPOUNDS

[75] Inventors: Satoshi Urano; Ryuzo Mizuguchi, both of Yawata, Japan

[73] Assignee: Nippon Paint Co., Ltd., Osaka, Japan

[21] Appl. No.: 220,887

[22] Filed: Jun. 16, 1988

Related U.S. Application Data

[63] Continuation of Ser. No. 71,582, Jul. 9, 1987, abandoned, which is a continuation of Ser. No. 821,232, Jan. 22, 1986, abandoned, which is a continuation of Ser. No. 674,741, Nov. 26, 1984, abandoned.

[30] Foreign Application Priority Data

Nov. 28, 1983 [JP] Japan .................................. 58-225226
Nov. 15, 1984 [JP] Japan .................................. 59-241876

[51] Int. Cl.$^5$ .......................................... C07C 145/02
[52] U.S. Cl. .................................................. 562/871
[58] Field of Search ........................ 560/336; 562/871

[56] References Cited

PUBLICATIONS

Die Makromolekulare Chemie, vol. 131, No. 3199, 1970, pp. 247-257, Staudinger Wagner & Zook, Synthetic Org. Chem. (1965), pp. 35-39.

*Primary Examiner*—Alan Siegel
*Attorney, Agent, or Firm*—Wegner & Bretschneider

[57] ABSTRACT

Production of an alkenoyl isocyanate of the formula:

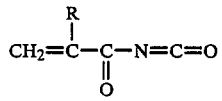

wherein R is a hydrogen atom or a lower alkyl group by reacting an acrylamide of the formula:

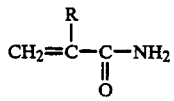

wherein R is as defined above with an oxalyl halide of the formula

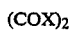

wherein X is a halogen atom to give a reaction mixture comprising a haloalkanoyl isocyanate of the formula:

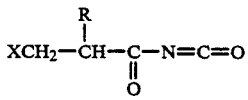

wherein R and X are each as defined above with or without the alkenoyl isocyanate, recovering the haloalkanoyl isocyanate and, when present, the alkenoyl isocyanate separately from the reaction mixture and reacting the recovered haloalkanoyl isocyanate with a hydrogen halide-eliminating agent to give the alkenoyl isocyanate.

14 Claims, No Drawings

PRODUCTION OF ISOCYANATE COMPOUNDS

This application is a continuation of U.S. application Ser. No. 071,582, filed July 9, 1987, now abandoned, which is a continuation of U.S. Pat. No. 821,232, filed Jan. 22, 1986, now abandoned, which is a continuation of U.S. Pat. No. 674,741, filed Nov. 26, 1984, now abandoned.

The present invention relates to production of isocyanate compounds. More particularly, it relates to production of alkenoyl isocyanates of the formula:

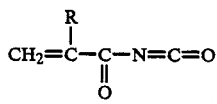 (I)

$$CH_2=\overset{R}{\underset{}{C}}-\underset{\underset{O}{\parallel}}{C}-N=C=O$$

wherein R is a hydrogen atom or a lower alkyl group (e.g. methyl, ethyl, propyl), particularly through haloalkanoyl isocyanates of the formula:

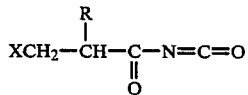 (II)

$$XCH_2-\overset{R}{\underset{}{CH}}-\underset{\underset{O}{\parallel}}{C}-N=C=O$$

wherein X is a halogen atom (e.g. chlorine, bromine) and R is as defined above.

Throughout the specification, the term "lower alkyl" is intended to mean alkyl having 1 to 5 carbon atoms, preferably 1 to 3 carbon atoms, more preferably methyl. The term "halogen" is intended to mean chlorine, bromine, iodine and fluorine, inclusively. Among them, preferred are chlorine and bromine, particularly chlorine.

In general, compounds having an isocyanate group are widely used in the field of polymer chemistry because of their excellent reactivity. Particularly, those having a polymerizable double bond and an isocyanate group in the molecule are expected to have great usefulness because the double bond and the isocyanate group can respectively participate in various reactions depending upon different reaction mechanisms. Specific examples are vinyl isocyanate (Angew. Chem., Int. Ed., 18, 319 (1979)), isocyanatoethyl methacrylate (Japanese Patent Publn. (unexamined) No. 5921/79), acryloyl isocyanate (Chem. Ber., 84, 4 (1951)), alpha-methylacryloyl isocyanate (Chem. Ber., 84, 4 (1951)), etc.

Among them, the alkenoyl isocyanates (I) such as acryloyl isocyanate (I: R =hydrogen) and alpha-methylacryloyl isocyanate (I: R =methyl) are particularly interesting in that the reactivities of the polymerizable double bond and the isocyanate group are enhanced by the carbonyl group present between them. Namely, the alkenoyl isocyanates (I) can undertake various reactions such as radical polymerization, anion polymerization, dimerization, trimerization, polar addition and addition of active hydrogen based on the partial structure (A) (i.e. conjugated double bond structure) and/or on the partial structure (B) (i.e. acylisocyanate structure) as set forth below and may be used as the industrial starting materials in various chemical fields:

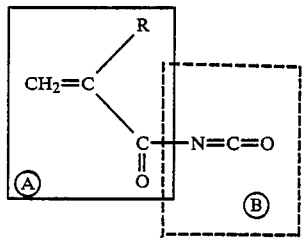

The alkenoyl isocyanates (I) were originally prepared by reacting the corresponding alkenoyl chlorides with silver isocyanate (Chem. Ber., 84, 4 (1951)). Apparently, this process is industrially disadvantageous in using an expensive reagent such as silver isocyanate. There is also known the process wherein isocyanic acid is used in place of silver isocyanate (U.S. Pat. No. 3,155,700). In this process, however, isocyanic acid is produced by heat decomposition of its trimer, i.e. isocyanuric acid, at such a high temperature as 620° C. In addition, isocyanic acid is a gaseous material. Accordingly, a special apparatus is needed, and handling of the gaseous material is troublesome.

In 1962 to 1965, Speziale et al developed a process for production of acyl isocyanates from amides by reacting the latter with oxalyl chloride (J. Org. Chem., 27, 3742 (1962); ibid., 23, 1805 (1963); ibid., 30, 4306 (1965)). When this process is applied to aromatic amides, the objective acylisocyanate compounds are usually obtainable in good yields. However, its application to aliphatic amides can not usually afford the objective acylisocyanate in noticeable yields.

In fact, the present inventors once attempted to produce acryloyl isocyanate (I: R =hydrogen) by reacting acrylamide with oxalyl chloride according to said Speziale et al process, but the objective acryloyl isocyanate could not be recovered from the reaction mixture. Although an effort to obtain the objective acryloyl isocyanate was made under various reaction conditions, no successful outcome could be obtained. Then, the present inventors applied the Speziale et al process to alpha-methylacrylamide in place of acrylamide and found surprisingly that alpha-methylacryloyl isocyanate (I: R =methyl) can be recovered from the reaction mixture in a noticeable yield. The subsequent study on said reaction mixture revealed that it includes a considerable amount of alpha-methyl-beta-chloropropionyl isocyanate (II: R =methyl; X =chlorine) in addition to alpha-methylacryloyl isocyanate, and alpha-methyl-beta-chloropropionyl isocyanate can be readily converted into alpha-methylacryloyl isocyanate by treatment with a hydrogen chloride-eliminating agent.

With the knowledge ascertained above, the reaction mixture between acrylamide and oxalyl chloride was then carefully examined, and as the result, its major product was confirmed to be beta-chloropropionyl isocyanate (II: R =hydrogen; X =chlorine), which is treated with a hydrogen chloride-eliminating agent to give acryloyl isocyanate (I: R =hydrogen).

In addition, it was confirmed that the reaction of acryloyl isocyanate (I: R =hydrogen) or alpha-methylacryloyl isocyanate (I: R =methyl) with hydrogen chloride gives beta-chloropropionyl isocyanate (II: R =hydrogen; X =chlorine) or alpha-methyl-beta-chloropropionyl isocyanate (II: R =methyl; X =chlorine).

On the basis of the above findings, the relationships as shown in Scheme I have now been established:

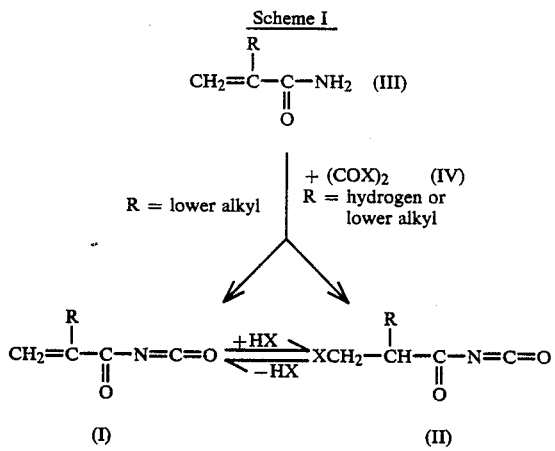

wherein R and X are each as defined above.

According to the present invention, there is provided a process for preparing the alkenoyl isocyanate (I) and/or the haloalkanoyl isocyanate (II) which comprises reacting the acrylamide (III) with the oxalyl halide (IV) (Reaction A). There is also provided a process for preparing the haloalkanoyl isocyanate (II) which comprises reacting the alkenoyl isocyanate (I) with hydrogen halide (Reaction B). There is further provided a process for preparing the alkenoyl isocyanate (I) which comprises reacting the haloalkanoyl isocyanate (II) with a hydrogen halide-eliminating agent (Reaction C).

Referring to Scheme I, each of Reactions A to C will be hereinafter explained in detail.

Reaction A:

The acrylamide (III) is reacted with the oxalyl halide (IV) to give the alkenoyl isocyanate (I) and/or the haloalkanoyl isocyanate (II).

The molar proportion of the acrylamide (III) and the oxalyl halide (IV) to be reacted may be usually 10–0.1:1, preferably 1–0.5:1. A reaction solvent is not necessarily required, but its use is normally preferred. As the reaction solvent, there may be used any inert solvent, particularly a halogenated hydrocarbon, of which specific examples are carbon tetrachloride, chloroform, dichloromethane, 1,1-dichloroethane, 1,2-dichloroethane, 1,6-dichlorohexane, 1,5-dichloropentane, 1,2-dichloropropane, 1,3-dichloropropane, 2,2-dichloropropane, 1,1,1-trichloroethane, 1,1,2-trichloroethane, 1,1,1,2-tetrachloroethane, 1,1,2,2-tetrachloroethane, 1,4-dichlorobutane, 2,3-dichlorobutane, 1-chlorobutane, 2-chlorobutane, chlorobenzene, chlorocyclohexane, ethylene tetrachloride, trichloroethylene, pentachloroethane, chloropropane, 1,2-dichloroethylene, o-, m- or p-dichlorobenzene, o-, m- or p-chlorotoluene, 1,2,4-trichlorobenzene, bromobenzene, bromoethane, 1- or 2-bromopropane, 1- or 2-bromobutane, 1- or 2-bromopentane, o-, m- or p-bromotoluene, bromocyclohexane, bromochloroethane, 1-bromohexane, etc. The reaction temperature may be ordinarily from −50° to 150° C., preferably from −30° to 100° C.

For isolation of the reaction product from the reaction mixture, there may be adopted any per se conventional separation procedure such as distillation under atmospheric or reduced pressure.

In the above reaction, the haloalkanoyl isocyanate (II) is the sole major reaction product when R is hydrogen. In case of R being lower alkyl, the alkenoyl isocyanate (I) and the haloalkanoyl isocyanate (II) are the major reaction products. Under usual reaction conditions, their proportion is nearly equal, and the rate of the alkenoyl isocyanate (I) has a tendency to increase with a lower reaction temperature. In order to enhance more or less the yield of the haloalkanoyl isocyanate (II), it is usually preferred to carry out the reaction in the presence of a hydrogen halide, particularly hydrogen chloride. The amount of the hydrogen halide may be normally not less than the equimolar amount, particularly excessive, to the acrylamide (III). For instance, the reaction may be effected while introducing gaseous hydrogen chloride into the reaction system. Separation between the alkenoyl isocyanate (I) and the haloalkanoyl isocyanate (II) may be accomplished with ease by a per se conventional separation procedure such as distillation under atmospheric or reduced pressure.

Reaction B:

The alkenoyl isocyanate (I) is reacted with hydrogen halide to give the haloalkanoyl isocyanate (II).

As the hydrogen halide, there may be used hydrogen chloride, hydrogen bromide, etc., preferably hydrogen chloride. While any reaction solvent is not necessarily required, the use of an inert solvent, particularly a halogenated hydrocarbon as exemplified in connection with Reaction A, is preferred. For instance, the alkenoyl isocyanate (I) may be dissolved in an appropriate inert solvent, followed by blowing gaseous hydrogen chloride therein. The reaction temperature is usually from −50° to 150° C., preferably from −10° to 100° C.

Separation of the reaction product from the reaction mixture may be carried out by a per se conventional separation procedure such as distillation under atmospheric or reduced pressure.

Reaction C:

The haloalkanoyl isocyanate (II) is reacted with a hydrogen halide-eliminating agent to give the alkenoyl isocyanate (I).

As the hydrogen halide-eliminating agent, there may be used not only a hydrogen halide-eliminating agent in a strict sense, i.e. the one to be used theoretically in at least an equimolar amount to the haloalkanoyl isocyanate (II), but also a hydrogen halide-eliminating catalyst, which may be employed in an amount smaller than the equimolar amount. Specific examples of the hydrogen halide-eliminating agent are amines such as triethylamine, 1,8-diazabicyclo[5.4.0]undecene-7, pyridine and quinoline, alkali metal or alkaline earth metal hydroxides such as sodium hydroxide, potassium hydroxide and magnesium hydroxide, metal oxides such as copper oxide, magnesium oxide, calcium oxide, alumina and iron oxide, metal complexes such as $(Ph_3P)_2Ru(CO)_3$ and $(PhP)_3Pt$ (wherein Ph is phenyl), metal halides such as lithium chloride, titanium chloride, aluminum chloride and sodium chloride, metal salts such as zinc naphthenate, nickel acetate, barium sulfate and potassium phosphate, metal alkoxides such as potassium t-butoxide, sodium ethoxide and sodium isopropoxide, synthetic zeolites such as molecular sieve and microporous glass, boric acid, oxirane, metal zinc, triphenyl phosphine, etc. Among them, particularly preferred are those chosen from amines, metal oxides, metal halides, synthetic zeolites, triphenyl phosphine, etc.

The reaction may be effected using the hydrogen halide-eliminating agent normally in an amount of 0.1 to 100 mol, preferably of 0.1 to 10 mol, to 1 mol of the haloalkanoyl isocyanate (II) in the presence or absence of an appropriate inert solvent. Specific examples of the inert solvent are an aliphatic hydrocarbon (e.g. pentane, hexane, heptane), an aromatic hydrocarbon (e.g. benzene, toluene, xylene), an alicyclic hydrocarbon (e.g. cyclohexane, methylcyclohexane, decalin), a hydrocarbon solvent (e.g. petroleum ether, petroleum benzin), a halogenated hydrocarbon solvent (e.g. carbon tetrachloride, chloroform, 1,2-dichloroethane), an ether solvent (e.g. ethyl ether, isopropyl ether, anisole, dioxane, tetrahydrofuran), a ketone (e.g. acetone, methyl ethyl ketone, methyl isobutyl ketone, cyclohexanone, acetophenone, isophorone), an ester (e.g. ethyl acetate, butyl acetate), acetonitrile, dimethylformamide, dimethylsulfoxide, etc. The reaction temperature may be usually from −50° to 200° C., preferably from 0° to 150° C.

Recovery of the reaction product from the reaction mixture may be accomplished by a per se conventional separation procedure such as distillation under atmospheric or reduced pressure.

In any of said Reactions A to C including the reaction and the post-treatment, a small amount of a polymerization inhibitor may be incorporated into the reaction system or the reaction mixture for prevention of the unnecessary polymerization on the double bond. Examples of the polymerization inhibitor are hydroquinone, p-methoxyphenol, 2,6-di-t-butyl-4-methylphenol, 4-t-butylcatechol, bisdihydroxybenzylbenzene, 2,2′-methylene-bis(6-t-butyl-3-methylphenol), 4,4′-butylidene-bis(6-t-butyl-3-methylphenol), 4,4′-thiobis(6-t-butyl-3-methylphenol), p-nitrosophenol, diisopropylxanthogenesulfide, N-nitrosophenylhydroxylamine ammonium salt, 1,1-diphenyl-2-picrylhydrazil, 1,3,5-triphenylpheldazyl, 2,6-di-t-butyl-alpha-(3,5-di-t-butyl-4-oxo-2,5-cyclohexadien-l-ylidene)-p-trioxy, 2,2,6,6-tetramethyl-4-piperidone-l-oxil, dithiobenzoyl sulfide, p,p′-ditolyl trisulfide, p,p′-ditolyl tetrasulfide, dibenzyl tetrasulfide, tetraethylthiuram disulfide, etc.

For preparation of the alkenoyl isocyanate (I), the acrylamide (III) may be reacted with the oxalyl halide (IV) according to Reaction A so that a reaction mixture comprising the haloalkanoyl isocyanate (II) in the case of R being hydrogen or a reaction mixture comprising the alkenoyl isocyanate (I) and the haloalkanoyl isocyanate (II) in the case of R being lower alkyl is produced. From the reaction mixture, the haloalkanoyl isocyanate (II) and, when present, the alkenoyl isocyanate (I) are recovered separately by a per se conventional separation procedure such as distillation under atmospheric or reduced pressure. The thus recovered haloalkanoyl isocyanate (II) is then reacted with the hydrogen halide-eliminating agent according to Reaction C to give the alkenoyl isocyanate (I).

The alkenoyl isocyanate (I) and the haloalkanoyl isocyanate (II) are, in general, liquids stable at room temperature and therefore can be handled with ease. They are soluble in various organic solvents and can be used in their solution form. When allowed to stand in the air, they are readily reacted with moisture in the air to give the corresponding amides. This property is meritorious from the viewpoint of environmental pollution. Their double bond or halogen atom is very reactive and can be readily reacted with other compounds to give isocyanate derivatives. Further, for instance, the alkenoyl isocyanate (I) exerts a strong antimicrobial activity in its gaseous state and therefore is useful as an antimicrobial agent. Furthermore, the alkenoyl isocyanate (I) can participate in various chemical reactions due to the functional groups present therein and therefore can be used for production of starting materials and intermediates in the fields of pharmaceuticals, agro-chemicals, dyestuffs, etc. Moreover, it has a wide use as a monomer for production of various polymers. For instance, its copolymerization with styrene, alkyl acrylate, alkyl methacrylate or the like affords varnish resin. Further, for instance, its copolymerization with other monomers affords polymers useful as dyestuffs, adhesives, dipping agents, foaming agents, fiber treating agents, etc.

Likewise, the haloalkanoyl isocyanate (II) is useful as a starting material or an intermediate in the production of pharmaceuticals, agro-chemicals, dyestuffs, thermosetting resins, hydrophilic resins, surfactants, etc.

In general, the isocyanate compounds wherein R is lower alkyl, e.g. alpha-methylacryloyl isocyanate and alpha-methyl-beta-chloropropionyl isocyanate, are more stable than the corresponding isocyanate compounds wherein R is hydrogen, e.g. acryloyl isocyanate and beta-chloropropionyl isocyanate, particularly when heated.

Practical and presently preferred embodiments of the invention are illustratively shown in the following Examples wherein part(s) and % are by weight unless otherwise indicated.

EXAMPLE 1

(Reaction (A))

To a suspension of methacrylamide (17.9 g) and hydroquinone (0.18 g) in chloroform (100 ml), a solution of oxalyl chloride (20 ml) in chloroform (15 ml) was dropwise added while ice-cooling at 0° C. under nitrogen stream. The resultant mixture was warmed to room temperature and stirred for 100 minutes. Hydroquinone (0.18 g) was added thereto, and the mixture was heated while stirring at 60° C. for 4 hours. After being allowed to cool, the resulting mixture was concentrated and distilled under reduced pressure to give a transparent liquid (22.2 g), which was further distilled under reduced pressure to give methylacryloyl isocyanate as a fraction boiling at 52°–53° C./39 mmHg.

EXAMPLE 2

(Reaction (A))

To a solution of oxalyl chloride (243 g; 1.92 mol) in 1,2-dichloroethane (350 ml), a solution of methacrylamide (106 g; 1.25 mol) in 1,2-dichloroethane (450 ml) was dropwise added in 50 minutes while ice-cooling at 0° C under nitrogen stream. The mixture was stirred at 0° C. for 2 hours, and stirring was continued under reflux for 2 hours. After being allowed to cool, the resultant mixture was concentrated and distilled under reduced pressure to give methacryloyl isocyante (63 g; yield, 45%) as a fraction boiling at 52°–53° C./39 mmHg (transparent liquid) and then alpha-methyl-beta-chloropropionyl isocyanate (75.4 g; yield, 40.9%) as a fraction boiling at 83°–85° C./39 mmHg (transparent liquid).

EXAMPLE 3

(Reaction (A))

To a solution of oxalyl chloride (95.25 g; 0.75 mol) in 1,2-dichloroethane (150 ml), a solution of acrylamide (35.5 g; 0.5 mol) and hydroquinone (0.54 g) in 1,2- dichloroethane (200 ml) was dropwise added in 30 minutes at −30° to 0° C. under nitrogen stream. The mixture was heated and stirred under reflux for 1 hours. After being allowed to cool, the resultant mixture was distilled under reduced pressure to give beta-chloropropionyl isocyanate (44.7 g) as a fraction boiling at 74°–75° C./25 mmHg (transparent liquid).

EXAMPLE 4

(Reaction (A))

Into a suspension of methacrylamide (106 g; 1.25 mol) in dichloroethane (600 ml), dry hydrogen chloride gas was blown while cooling with ice for about 1 hour. Then, oxalyl chloride (243.9 g; 1.92 mol) was dropwise added thereto while continuing hydrogen chloride blowing and ice cooling. The resultant mixture was heated to reflux, and the refluxing was continued for 30 minutes. After being allowed to cool, the reaction mixture was distilled under reduced pressure to give alpha-methyl-beta-chloropropionyl isocyanate.

EXAMPLE 5

(Reaction (B))

Hydrogen chloride gas was introduced into a solution of methacryloyl isocyanate (4.26 g; 38 mmol) in chloroform (30 ml) at 10°–12° C. while cooling with water. Hydrogen chloride gas was further introduced therein while heating under reflux for one hour. After being allowed to cool, the resulting mixture was distilled under reduced pressure to give alpha-methyl-beta-chloropropionyl isocyante (3.26 g; yield, 58 %) as a fraction boiling at 83°–85° C./39 mmHg (transparent liquid). In addition, there was recovered the starting methacryloyl isocyanate (1.6 g).

EXAMPLE 6

(Reaction (C))

To a solution of alpha-methyl-beta-chloropropionyl isocyanate (14.75 g; 100 mmol) in toluene (20 ml), molecular sieve 4A (20 g) was added, and the mixture was heated under reflux for 13.5 hours under nitrogen stream. After being allowed to cool, the molecular sieve was collected by filtration, and the filtrate was distilled under reduced pressure to give methacryloyl isocyanate (3.55 g). In addition, there was recovered the starting alpha-methylbeta-chloropropionyl isocyanate (3.54 g).

EXAMPLE 7

(Reaction (C))

In the same manner as in Example 6 but not using toluene, the reaction was carried out, whereby methacryloyl isocyanate as in Example 6 was obtained.

EXAMPLE 8

(Reaction (C))

In the same manner as in Example 6 but using beta-chloropropionyl isocyanate instead of alpha-methyl-beta-chloropropionyl isocyanate, the reaction was carried out, whereby acryloyl isocyanate was obtained. B.P., 82°–83° C.

What is claimed is:

1. A process for preparing acryloyl isocyanate, which comprises (a) reacting acrylamide with an oxalyl halide in a hydrogenated hydrocarbon at a temperature of −50° to 150° C. to give a reaction mixture comprising beta-halopropionyl isocyanate, (b) recovering beta-halopropionyl isocyanate from the reaction mixture by distillation and (c) reacting the recovered beta-halopropionyl isocyanate with a hydrogen halide-eliminating agent at a temperature of −50° to 200° C. to give acryloyl isocyanate.

2. The process according to claim 1, wherein the reaction in the step (a) is carried out in the presence of a polymerization inhibitor.

3. The process according to claim 1, wherein the reaction in the step (a) is carried out at a temperature of −30° to 100° C.

4. The process according to claim 1, wherein the distillation in the step (b) is carried out in the presence of a polymerization inhibitor.

5. The process according to claim 1, wherein the distillation in the step (b) is carried out under reduced pressure.

6. The process according to claim 1, wherein the reaction in the step (c) is carried out in the presence of a polymerization inhibitor.

7. The process according to claim 1, wherein the reaction in the step (c) is carried out at a temperature of 0° to 150° C.

8. A process for preparing methacryloyl isocyanate, which comprises (a) reacting methacrylamide with an oxalyl halide at a temperature of −50° to 150° C. to give a reaction mixture comprising methacryloyl isocyanate and beta-halo-alpha-methyl-propionyl isocyanate, (b) recovering methacryloyl isocyanate and beta-halopropionyl isocyanate separately from the reaction mixture by distillation and (c) reacting the recovered beta-halo-alpha-methyl-propionyl isocyanate with a hydrogen halide-eliminating agent at a temperature of −50° to 200° C. to give methacyloyl isocyanate.

9. The process according to claim 8, wherein the reaction in the step (a) is carried out in the presence of a polymerization inhibitor.

10. The process according to claim 8, wherein the reaction in the step (a) is carried out at a temperature of −30° to 100° C.

11. The process according to claim 8, wherein the distillation in the step (b) is carried out in the presence of a polymerization inhibitor.

12. The process according to claim 8, wherein the distillation in the step (b) is carried out under reduced pressure.

13. The process according to claim 8, wherein the reaction in the step (c) is carried out in the presence of a polymerization inhibitor.

14. The process according to claim 8, wherein the reaction in the step (c) is carried out at a temperature of 0° to 150° C.

* * * * *